(12) United States Patent
Seo et al.

(10) Patent No.: US 10,653,559 B2
(45) Date of Patent: May 19, 2020

(54) SHADING GOGGLES HAVING FUNCTION OF DOUBLE PROTECTION

(71) Applicant: SERVORE CO., LTD., Gyeonggi-do (KR)

(72) Inventors: Woon Su Seo, Gyeonggi-do (KR); Jeong Min Seo, Gyeonggi-do (KR)

(73) Assignee: SERVORE CO., LTD., Gyeonggi-do (KR)

( * ) Notice: Subject to any disclaimer, the term of this patent is extended or adjusted under 35 U.S.C. 154(b) by 0 days.

(21) Appl. No.: 16/004,602

(22) Filed: Jun. 11, 2018

(65) Prior Publication Data

US 2018/0360662 A1    Dec. 20, 2018

(30) Foreign Application Priority Data

Jun. 15, 2017    (KR) .................. 10-2017-0075755

(51) Int. Cl.
*A61F 9/02*    (2006.01)
*G02F 1/1333*    (2006.01)

(52) U.S. Cl.
CPC .............. *A61F 9/028* (2013.01); *A61F 9/022* (2013.01); *G02F 1/133308* (2013.01); *G02F 2001/13332* (2013.01); *G02F 2001/133311* (2013.01); *G02F 2001/133314* (2013.01); *G02F 2001/133331* (2013.01); *G02F 2201/50* (2013.01)

(58) Field of Classification Search
CPC .... A61F 9/022; A61F 9/028; G02F 1/133308; G02F 2001/133314; G02F 2001/13332

USPC .......................................................... 349/14
See application file for complete search history.

(56) References Cited

U.S. PATENT DOCUMENTS

| | | | |
|---|---|---|---|
| 6,718,561 B2* | 4/2004 | Dondero ................. | A61F 9/025 2/436 |
| 2013/0235323 A1* | 9/2013 | Sotzing .................... | C09K 9/02 351/44 |
| 2014/0259252 A1* | 9/2014 | Seo ......................... | A61F 9/022 2/8.2 |

FOREIGN PATENT DOCUMENTS

KR    20140111730    9/2014

* cited by examiner

*Primary Examiner* — Nathanael R Briggs
*Assistant Examiner* — William D Peterson
(74) *Attorney, Agent, or Firm* — IPLA P.A.; James E. Bame

(57) ABSTRACT

Shading goggles having a function of double protection comprises a goggle body having an LCD lens panel therein for protecting the eyes of a worker by blocking harmful light, and a soft skirt coupled to the rear side of the goggle body and being worn on a worker with an end being in close contact with the face of the worker to for an inside space, the goggles further comprises a protective lens having a gasket continuously disposed around the edge of the front side thereof and pressed on the rear side of the LCD lens panel and having an anti-fogging coating layer on the rear side exposed to the space.

9 Claims, 8 Drawing Sheets

SHADING GOGGLES HAVING FUNCTION OF DOUBLE PROTECTION

CROSS REFERENCE

The present application claims priority to Korean Patent Application No. 10-2017-0075755, filed 15 Jun. 2017, the entire contents of which is incorporated herein for all purposes by this reference.

BACKGROUND

The present invention relates to shading goggles having a function of double protection and, more particularly, to shading goggles having a function of double protection, the goggles preventing fogging inside by circulating external air through vents formed in a goggle body and preventing damage to an expensive LCD lens panel by doubly preventing foreign substances from entering the vents.

Generally, the welding is a technique of jointing same or different kinds of metal materials by partially applying a heat and a pressure to them at the same time. During the welding, since a strong light (arc) is emitted and broken pieces are generated, where the worker's eye is exposed to the strong light, it can cause loss of vision of the worker and inflict an injury on his eyeball etc. owing to the broken pieces.

Accordingly, in industrial settings, the work wears a welding helmet for protecting the eyeball and faces thereof from the strong light or broken pieces generated during the welding operation or cutting operation etc.

FIG. 1 is a view showing a shading goggle for welding of Korean Patent Registration No. 10-1482166 filed on 2013 by the present applicant. In this conventional shading goggle (10) for welding, a skirt part (20), which is coupled to a rear end portion thereof, is adhered to the worker's face, so that it prevents a harmful light, a welding spatter, a grinding particulate matter, or a fume gas etc. from being flowed therein.

In addition, as described above, since the heat generated from the worker's eye gets out of the inside thereof, a condensation can be generated in the LCD lens (30). Accordingly, a ventilation opening (40) capable of allowing the air to be flowed therein toward the LCD lens (30) is formed on a front side of the shading goggle (10), so that it can allow the air to be circulated to the inside of the shading goggle (10), thereby preventing the condensation through an air circulation.

However, besides the air, a large foreign matter such as the welding spatter or the grinding particulate matter etc. generated during welding can be flowed therein through the ventilation opening (40). Thus, if the hot welding spatter is entered into the inside of the eyes of the worker, it can cause a great damage to lose his sight. In addition, the foreign matter having large particles is scattered on the surface of the expensive LCD lens (30), so that a scratch is generated, thereby causing the damage of the LCD lens (30).

Also, the ventilation opening (40) serves to circulate the heat, which is generated in the inside thereof through the heat of the worker's eye, to outside thereof. However, since the air can be flowed therein in reverse, the fogging is generated in the LCD lens (30). Also, the welding fumes having small particles can be flowed therein in reverse through the ventilation opening (40), so that the LCD lens (30) is opaque, thereby causing a difficult work.

Accordingly, in order to overcome the problems of the conventional shading goggle for welding, the demand of the shading goggle for welding capable of allowing the air to be flowed in through the ventilation opening, preventing the foreign matter to be penetrated therein, and preventing the fogging of the internal LCD lens has been increased.

SUMMARY OF THE INVENTION

The present invention has been made in an effort to solve the problems and an object of the present invention is to primarily filter out large particles of foreign substances to prevent them from moving inside through vents, is to secondarily protect an LCD lens by filtering out small particles of foreign substances, and is to prevent the LCD lens from being fogged and being covered with dust.

According to one aspect of the present invention so as to accomplish these objects, there is provided to shading goggles having a function of double protection comprising a goggle body having an LCD lens panel therein for protecting the eyes of a worker by blocking harmful light, and a soft skirt coupled to the rear side of the goggle body and being worn on a worker with an end being in close contact with the face of the worker to for an inside space, wherein the goggle body has a vent unit allowing external air to flow inside the goggle body through vents formed at a side through the outer side of the goggle body such that the external air flowing inside circulates into the space through air vent holes formed inside the goggle body, and mesh filters are disposed in the vents to prevent external foreign substances from entering, and the goggles further comprises a protective lens having a gasket continuously disposed around the edge of the front side thereof and pressed on the rear side of the LCD lens panel and having an anti-fogging coating layer on the rear side exposed to the space.

Preferably, fitting protrusions fitted in the air holes extend from the edge of the protective lens, so the fitting protrusions are detachably fitted in the air holes.

Preferably, a slit is formed at a side of an end of the protective lens to be held by a user.

Preferably, the goggle body includes a front cover body having a window cut for the LCD lens panel; and a rear cover body having a window cut for the LCD lens panel and coupled to the rear side of the front cover body, the LCD lens panel is fixed between the front cover body and the rear cover body, and the air vent holes are formed around the edge of the window of the rear cover body so that external air flows toward the rear side of the LCD lens panel.

Preferably, a first retainer for seating a side of the front side of the LCD lens panel is formed inside the front cover body and a second retainer for seating a side of the rear side of the LCD lens panel is formed at a side of the front side of the rear cover body, whereby the LCD lens panel is seated in the first and second retainers between the front cover body and the rear cover body, and a predetermined number of fitting protrusions that protrude forward from an end of the window of the rear cover body are formed around the edge of the window and the air holes are formed between the fitting protrusion and the LCD lens panel.

BRIEF DESCRIPTION OF DRAWINGS

The above and other objects, features and advantages of the present invention will be more apparent from the following detailed description taken in conjunction with the accompanying drawings, in which.

DETAILED DESCRIPTION OF THE PREFERRED EMBODIMENT

Figure 1:
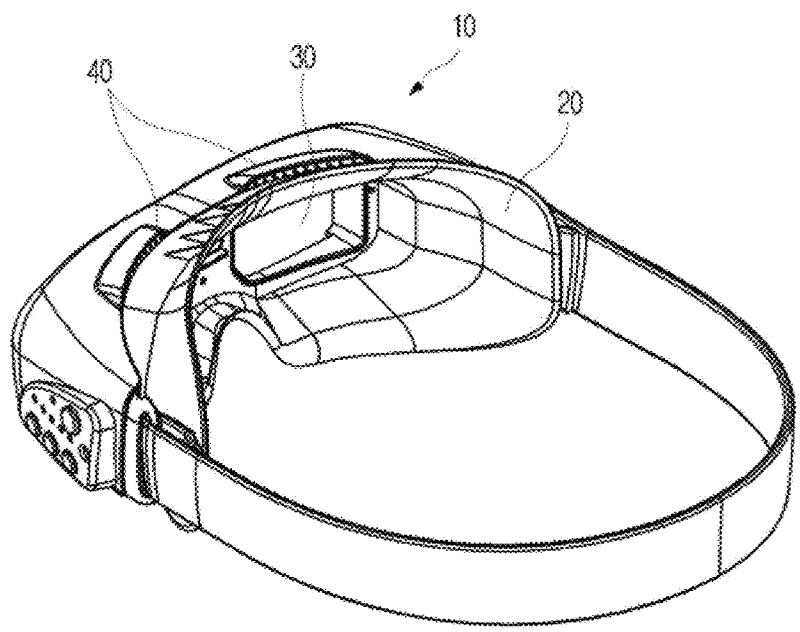
FIG. 1 is a view showing a shading goggle for welding.

Hereinafter, in order to fully understand the present invention, exemplary embodiments of the present invention are described with reference to the accompanying drawings.

The present invention can be modified in various forms, and the scope of the present invention should not be interpreted as being limited to the embodiment described in detail below. The present invention is provided to more completely explain the present invention to those skilled in the art.

Accordingly, the shape and the like of the elements expressed in the drawings may be exaggerated in order to emphasize a clearer description. It should be noted that the same elements in each figure are denoted by the same reference numerals. In addition, detailed descriptions of well-known functions and configurations deemed to obscure the gist of the present invention are omitted.

Hereinafter, a preferred embodiment according to the present invention will be described in detail with reference to the accompanying drawings.

Figure 2:
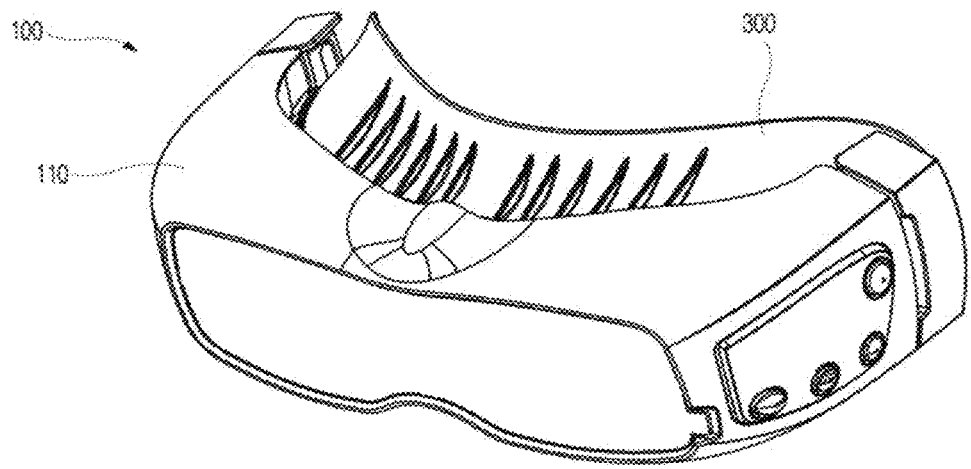
FIGS. 2 and 3 are perspective views showing shading goggles having a function of double protection according to the present invention.
Figure 3:
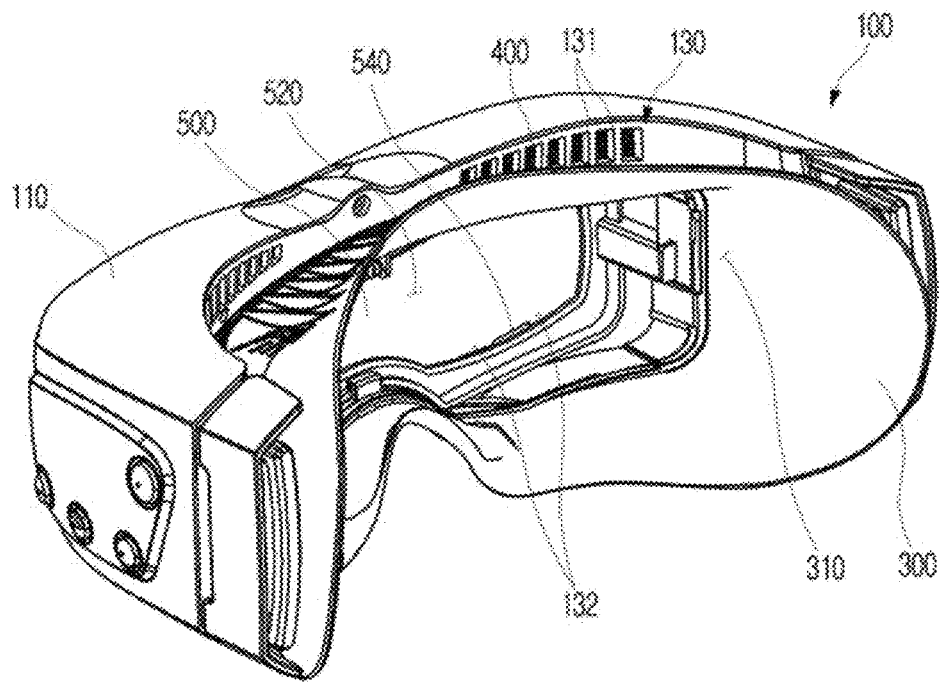
Figure 4:
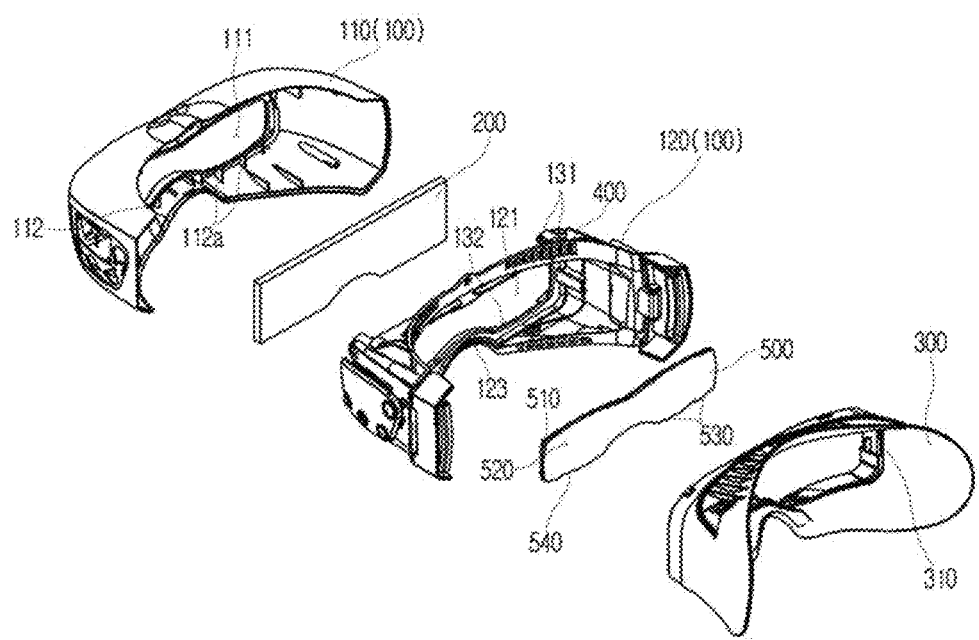
FIGS. 4 and 5 are exploded perspective views of the shading goggles having a function of double protection according to the present invention.
Figure 5:
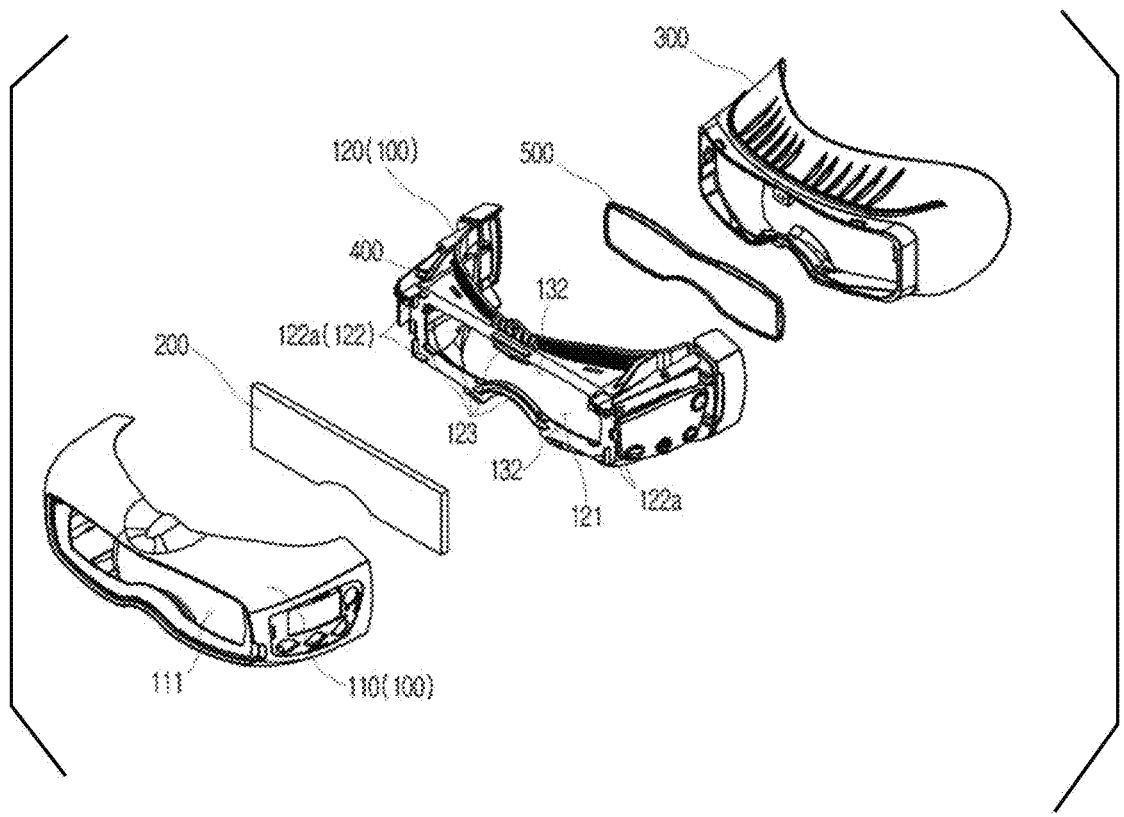
Figure 6:
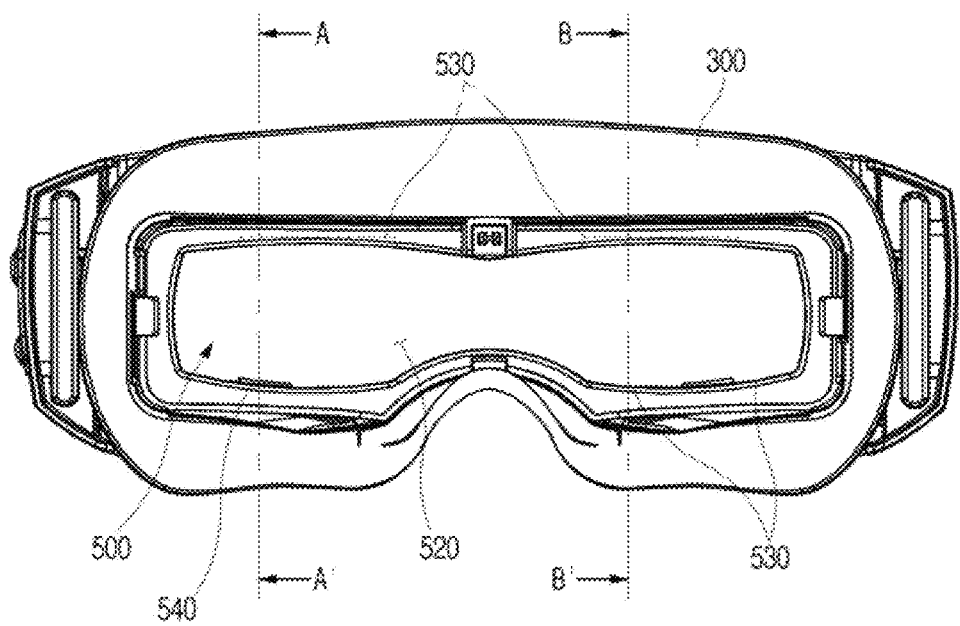
FIG. 6 is a view showing the rear side of the shading goggles having a function of double protection according to the present invention.
Figure 7:
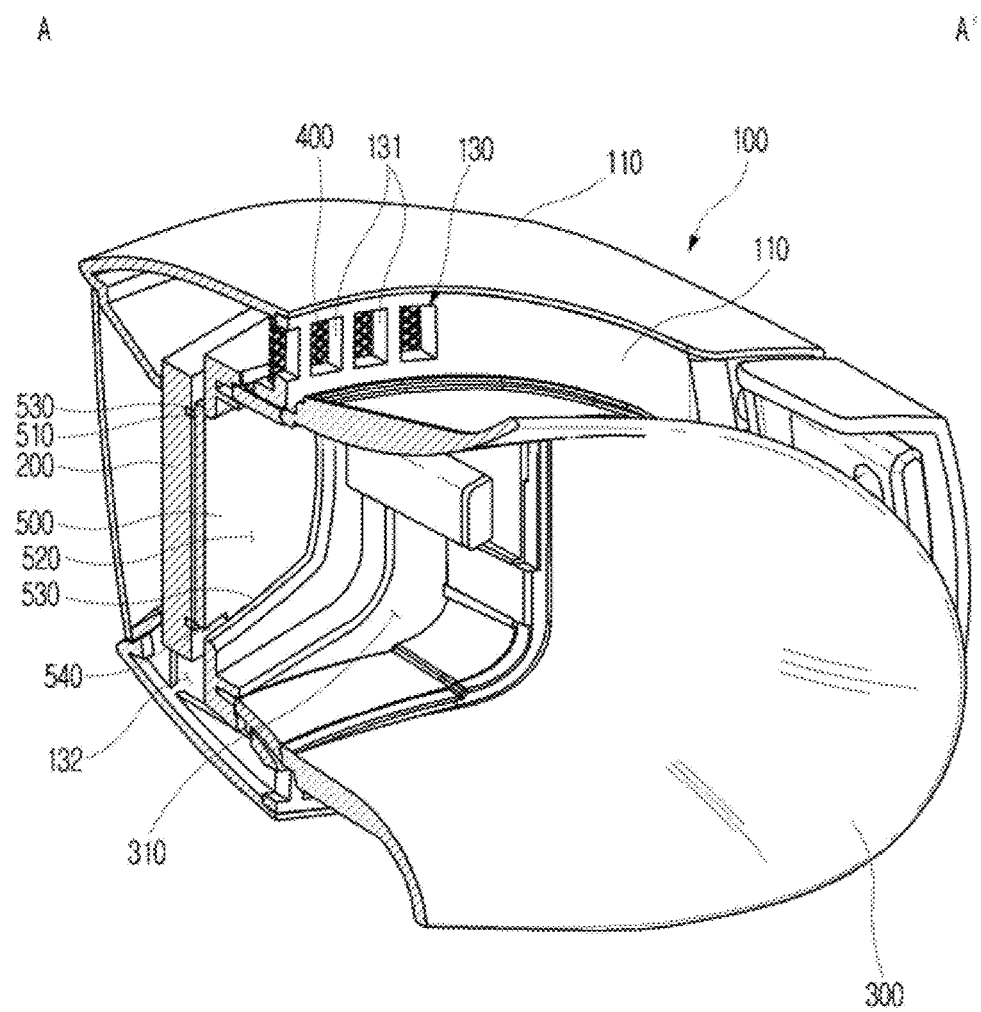
FIG. 7 is a cross-sectional view taken along line A-A' of FIG. 6.
Figure 8:
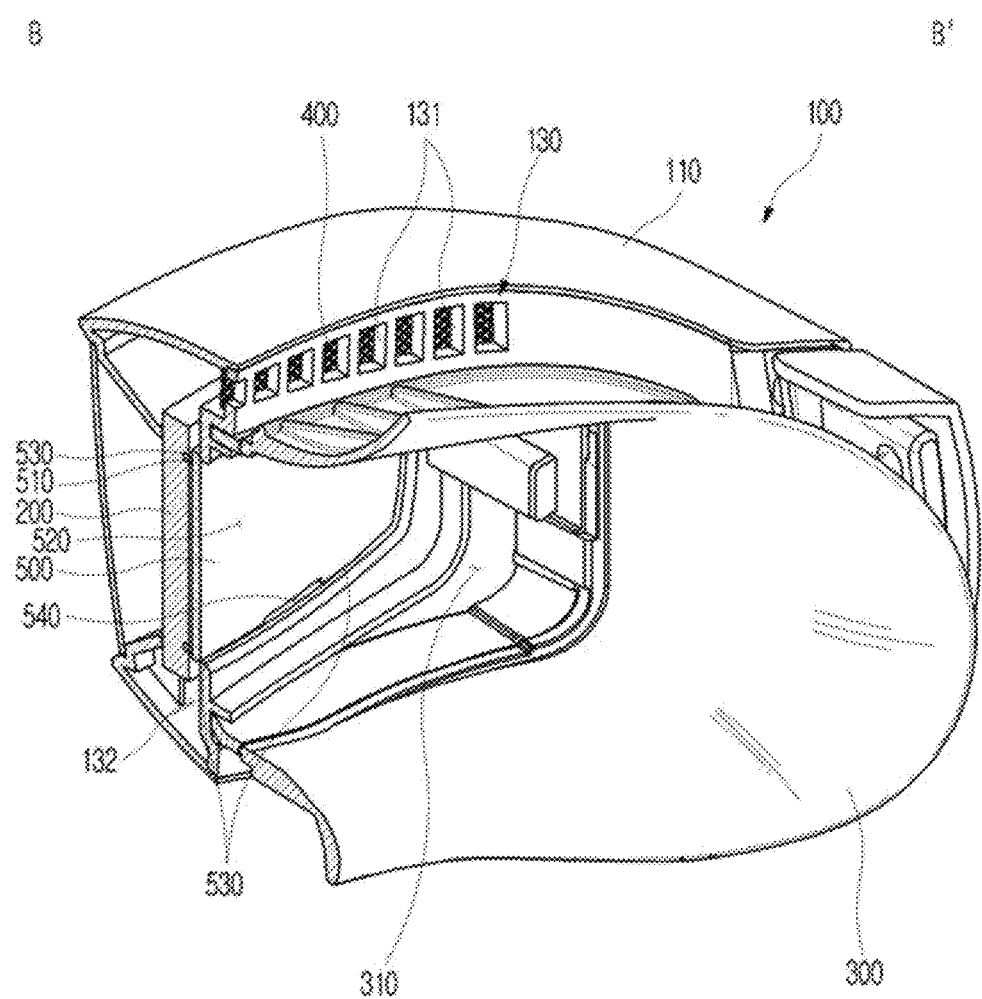
FIG. 8 is a cross-sectional view taken along line B-B' of FIG. 6.
Figure 9:
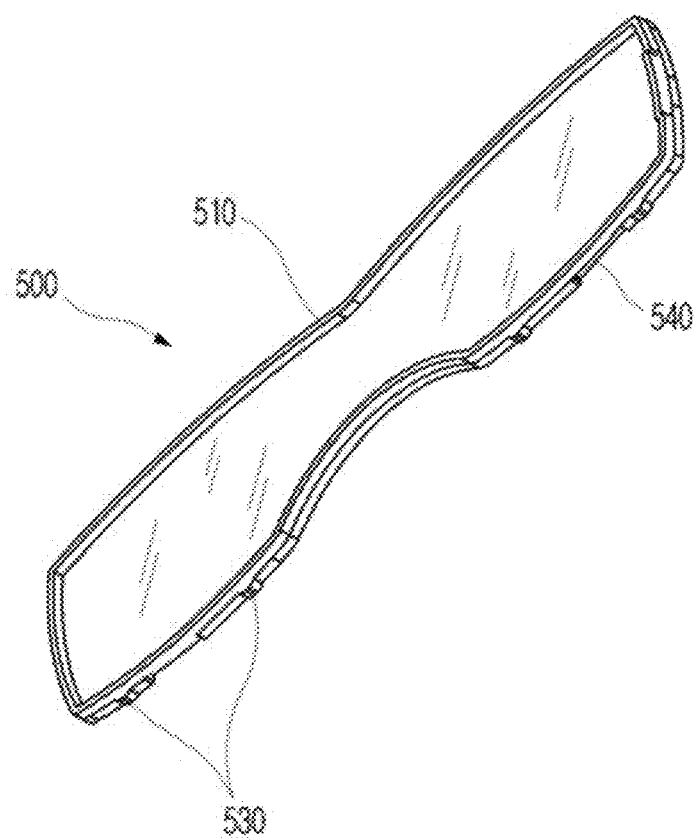
FIG. 9 is a perspective view showing the rear side of a protective lens according to the present invention.
Figure 10:
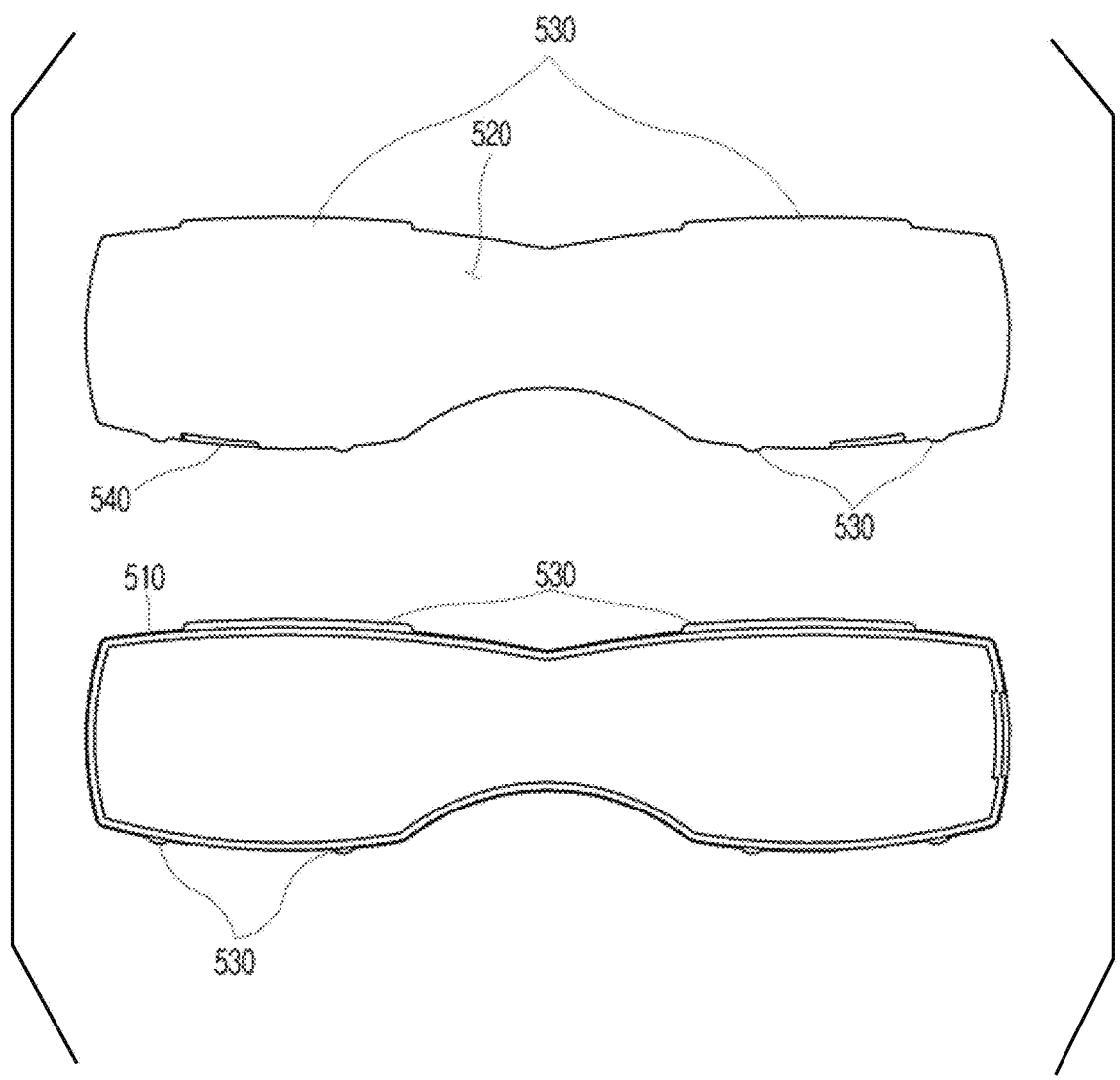
FIG. 10 is a view showing the front side and the rear side of the protective lens according to the present invention.

FIGS. 2 and 3 are perspective views showing shading goggles having a function of double protection according to the present invention, FIGS. 4 and 5 are exploded perspective views of the shading goggles having a function of double protection according to the present invention, FIG. 6 is a view showing the rear side of the shading goggles having a function of double protection according to the present invention, FIG. 7 is a cross-sectional view taken along line A-A' of FIG. 6, FIG. 8 is a cross-sectional view taken along line B-B' of FIG. 6, FIG. 9 is a perspective view showing the rear side of a protective lens according to the present invention, and FIG. 10 is a view showing the front side and the rear side of the protective lens according to the present invention.

Referring to the figures, shading goggles having a function of double protection according to the present invention includes a goggle body (100), a skirt (300), and a protective lens (500).

An LCD lens panel (200) for protecting the eyes of a worker by blocking harmful light is disposed inside the goggle body (100), the goggle body (100) includes a front cover body (110) and a rear cover body (120), and a vent unit (130) is formed at a side of the goggle body (100) to circulate external air through the inside.

A window (111) for seating the LCD lens panel (200) is formed through the front cover body (110) and a first retainer (112) for seating a side of the front of the LCD lens panel (200) is formed inside the front cover body (110). The first retainer (112) is composed of a plurality of ribs (112a) protruding over and under the window (111) and the front, top, and bottom of the LCD lens panel (200) is seated on L-shaped surface of the ribs (112a).

The rear cover body (120) is coupled to the rear side of the front cover body (110), has an inside space for mounting electronic devices and external air flowing inside, and has a window (121) for the LCD lens panel (200), the same as the front cover body (110).

A second retainer (122) for seating the LCD lens panel (200) is formed on the front side of the rear cover body (120) and has a plurality of fitting guide protrusions (122a) at positions corresponding to the edge of the LCD lens panel (200) on the front side of the cover body (120), so the edge of the LCD lens panel (200) is fitted inside the fitting guide protrusions (122a).

Further, a plurality of locking protrusions (123) that protrudes forward is formed around the window (121) on the front side of the rear cover body (120) and a side of the rear side of the LCD lens panel (200) is in close contact with the ends of the locking protrusions (123), so the LCD lens panel (200) is fixed in close contact between the front cover body (110) and the rear cover body (120).

The locking protrusions (123) are formed only at the top and bottom and the left and right corners around the edge of the window (121), and predetermined gaps are formed at the portions without the locking protrusions (123) between the LCD lens panel (200) and the window (121). The gaps are air vent holes (132) of a vent unit (130) to be described below. That is, the air vent holes (132) are formed over and under and at the left and right of the window (121) of the rear cover body (120).

The skirt (300), which is made of soft rubber, is coupled to the rear side of the goggle body (100), that is, the rear portion of the rear cover body (120) and has an end shaped similar to the outline of the face of a worker. Accordingly, when a worker wears the goggles, the end of the skirt (300) comes in close contact with the face of the worker and a closed space (310) is defined inside the skirt (300). The eyes are positioned in the space (310).

The vent unit (130) allows external air to flow inside the goggle body (100) through the vents (131) formed at a side through the outer side of the goggle body (100). The external air flowing inside circulates into the space (310) through the air vent holes (132) formed inside the goggle body (100).

In the present invention, a plurality of vents (131) is arranged in the longitudinal direction at the upper and lower portions of the rear cover body (120) and mesh filters (400) are disposed in the vents (131) to prevent permeation of external foreign substances. The mesh filters (400) prevent welding spatters produced by welding or grinding fragments produced by grinding from flying into the goggle body (100).

Further, in the present invention, the air vent holes (132) are formed along the edge of the window (121) of the rear cover body (120), so the external air flowing inside through the vents (131) flows rearward to the LCD lens panel (200).

The protective lens (500) is attached to the rear side of the LCD lens panel (200) to be detachable from the goggle body (100) in order to immediately deal with situations in welding and grinding work sites, thereby protecting the LCD lens panel (200) and preventing the LCD lens panel (200) fogging up.

An elastic gasket (510) having a predetermined thickness is continuously fitted on the edge of the front side of the protective lens (500). The gasket (510) is pressed to the rear side of the LCD lens panel (200) to function as a sealing with the thickness changed to preventing moisture and external air from flowing into the space between the rear side of the LCD lens panel (200) and the front side of the protective lens (500).

An anti-fogging coating layer (520) is separately formed on the rear side of the protective lens (500) to prevent fogging on the surface due to the temperature difference between the inside of the space (310) and the outside.

Fitting protrusions (530) extend from the edge of the protective lens (500) at positions corresponding to the air vent holes (132) formed at the upper and lower portions of the rear cover body (120) so that the gasket (510) is brought in close contact with the rear side of the LCD lens panel (200) by inserting the fitting protrusions (530) into the air vent holes (132). Further, a slit (540) cut inward is formed at a side of an end of the protective lens (500) so that a worker can easily put a finger into the slit (540) and take out the protective lens (500).

The method of using the shading goggles having a function of double protection according to the present invention is described in detail hereafter.

Figure 11:
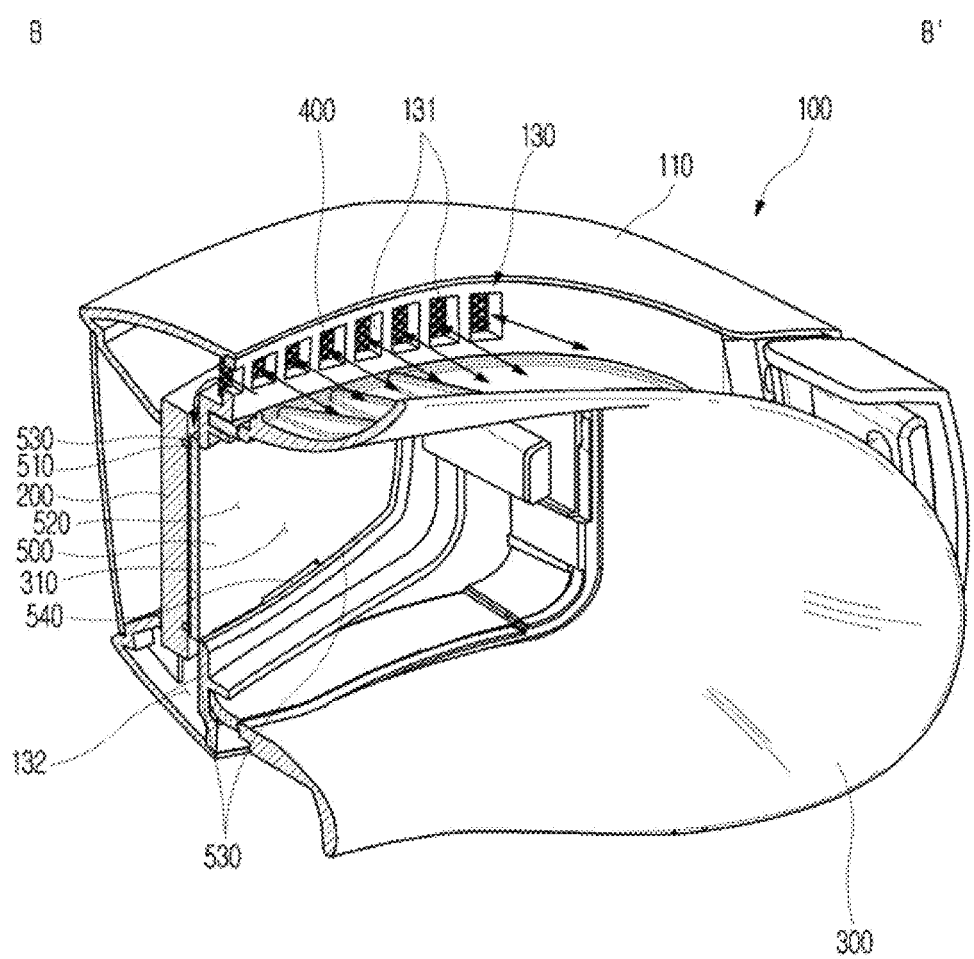
FIG. 11 is a cross-sectional view showing a path through which external air flows into the space when a worker wears the shading goggles having a function of double protection according to the present invention.

FIG. 11 is a cross-sectional view showing a path through which external air flows into the space when a worker wears the shading goggles having a function of double protection according to the present invention.

Referring to the figure, when a worker wears the shading goggles according to the present invention, external air or foreign substances cannot enter the space (310) inside the skirt (300) and external air circulates into the space (310) through the separate vent unit (130) formed at the goggle body (100).

In the present invention, the mesh filters (400) are disposed in the vents (131) disposed over and under the LCD lens panel (200), so large particles of foreign substances such as welding spatters produced by welding or grinding fragments produced by grinding are primarily prevented from entering the inside of the goggle body (100) through the mesh filters (400) while external air primarily circulates through the vents (131), thereby protecting the eyes of a worker and preventing damage to the surface of the expensive LCD lens panel (200).

However, fine particles such as welding fumes produced by welding are not filtered out by the mesh filters (400) and enter the space (310), and the welding fumes stick to the surface of the LCD lens panel (200) and make the visual field hazy. Accordingly, in the present invention, the gasket (510) attached to the rear side of the LCD lens panel (200) functions as a sealing, thereby preventing small particles of foreign substances such as welding fumes from entering to the inside of the LCD lens panel (200).

Further, external air with moisture cannot enter the inside the LCD lens panel (200) by sealing of the gasket (510), thereby preventing the LCD lens panel (200) from fogging.

As described above, in order to prevent fogging due to the heat from the eyes of a worker, external air is circulated inside through the vent unit (130) and foreign substances entering inside with the external air are primarily and secondarily filtered out through the mesh filters (400) and the gasket (510) of the protective lens (500), thereby preventing damage to the LCD lens panel (200).

Further, according to the present invention, the anti-fogging coating layer (520) is formed on the rear side of the protective lens (500) to prevent fogging due to backflow of external air. Further, the protective lens (500) is mounted in the air vent holes (132), so it is possible to freely minimize external air flowing backward through the air vent holes (132) by attaching/detaching the protective lens (500), depending on the situations of work sites.

According to the present invention, the LCD lens panel is prevented from fogging by circulating external air through the vents, thereby improving workability. Further, since the mesh filters are disposed in the vents, large particles of foreign substances such as welding spatters or grinding fragments are primarily filtered out and fine particles of foreign substances such as welding fumes are secondarily are prevented from entering to the inside of the LCD lens panel by the gasket being in close contact with the LCD lens panel, thereby protecting the worker's eyes, improving safety in working, preventing damage to the expensive LCD lens panel, and increasing the lifespan of the product.

Further, it is possible to freely control the amount of external air flowing back into the air vent holes by detachably mounting the protecting lens in the air vent holes in order to adaptably deal with fogging that may occur on a lens surface, depending on the situation of work sites.

While the present invention has been described with respect to the specific embodiments, it will be apparent to those skilled in the art that various changes and modifications may be made without departing from the spirit and scope of the invention as defined in the following claims.

What is claimed is:

1. Shading goggles having a function of double protection, comprising:
   a goggle body having an LCD lens panel therein for protecting the eyes of a worker by blocking harmful light; and
   a soft skirt coupled to the rear side of the goggle body and being worn on a worker with an end being in close contact with the face of the worker to form an inside space,
   wherein the goggle body has a vent unit allowing external air to flow inside the goggle body through vents formed through the outer side of the goggle body so the external air flowing inside circulates into the space through air vent holes formed inside the goggle body, and mesh filters are disposed in the vents to prevent external foreign substances from entering; and
   wherein the goggle body has a front cover body having a window cut for the LCD lens panel, and a rear cover body having a window cut for the LCD lens panel and coupled to the rear of the front cover body;
   wherein the LCD lens panel is fixed between the front cover body and the rear cover body;
   wherein the air vent holes are formed around the edge of the window of the rear cover body so the external air flows toward the rear side of the LCD lens panel;
   wherein the goggles include a protective lens formed on the rear side of the LCD lens panel and having an anti-fogging coating layer on the rear side exposed to the space;
   wherein a first retainer for seating a side of the front side of the LCD lens panel is formed inside the front cover body and a second retainer for seating a side of the rear side of the LCD lens panel is formed at a side of the front side of the rear cover body, whereby the LCD lens panel is seated in the first and second retainers between the front cover body and the rear cover body; and
   a predetermined number of fitting protrusions that protrude forward from an end of the window of the rear cover body are formed around the edge of the window and the air holes are formed between the fitting protrusion and the LCD lens panel.

2. Goggles, comprising:
a goggle body including
> a front cover having a front window,
> a rear cover having a rear window for coupling to rear side of the front cover,
> a lens disposed between the front window and the rear window,
> the rear cover having a plurality of protrusions disbursed around front of the rear window with each protrusion corresponding to edge of the lens so the lens is fitted within the protrusions, and
> front of the rear window having a plurality of gaps with each gap positioned, respectively, between two of the plurality of protrusions and corresponding to the edge of the lens with the plurality of gaps allowing external air to flow into the goggle body; and a skirt coupled to rear of the rear cover.

3. The goggles of claim 2, further comprising:
a protective lens releasably attached to rear of the lens.

4. The goggles of claim 3, wherein the protective lens comprises an anti-fogging coating layer on the rear side of the protective lens.

5. The goggles of claim 4, wherein the goggle body comprises a slit formed in the goggle body to correspond to an end of the protective lens for removal of the protective lens through the slit.

6. The goggles of claim 2, wherein the goggle body comprises vents for allowing the external air to flow into the goggle body.

7. The goggles of claim 6, wherein the vents are covered respectively by a filter to substantially prevent entry of external foreign substances into the goggle body.

8. The goggles of claim 2, wherein the plurality of protrusions comprises a plurality of fitting guide protrusions.

9. The goggles of claim 2, wherein the plurality of protrusions comprises a plurality of locking protrusions.

* * * * *